United States Patent [19]

White

[11] 4,194,05
[45] Mar. 18, 198

[54] PROCESS FOR PREPARING ESTERS OF α-ACETYL-α'-METHYLSUCCINIC ACID AND ESTERS OF α-METHYL-α'-ACETYL-α'-(5-METHYL-3-OXOHEXYL)SUCCINIC ACID

[75] Inventor: David R. White, Kalamazoo, Mich.
[73] Assignee: The Upjohn Company, Kalamazoo, Mich.
[21] Appl. No.: 938,972
[22] Filed: Sep. 1, 1978

Related U.S. Application Data

[63] Continuation-in-part of Ser. No. 778,571, Mar. 17, 1977, abandoned.

[51] Int. Cl.$^2$ .................... C07C 67/30; C07C 69/67
[52] U.S. Cl. ..................... 560/176; 560/126; 560/181; 562/479; 562/496; 562/508
[58] Field of Search ........................... 560/176

[56] References Cited

U.S. PATENT DOCUMENTS

| | | | |
|---|---|---|---|
| 2,797,237 | 6/1957 | Birbiglia et al. | 560/174 |
| 3,816,533 | 6/1974 | Brandstrom | 560/174 |
| 4,096,177 | 6/1978 | Baiocchi | 560/176 |

*Primary Examiner*—Vivian Garner
*Attorney, Agent, or Firm*—John T. Reynolds

[57] ABSTRACT

A diester of α-acetyl-α'-methyl succinic acid is pi pared in improved yield under substantially anhydro process conditions which minimizes decomposition that diester by reacting an acetoacetate ester with α-halopropionate ester in a solvent containing a nonp lar, aprotic liquid at from about 50° C. to reflux tempe ature in the presence of a phase transfer agent, a ca lytic amount of iodide ion and solid form, substantial anhydrous alkali metal base or basic salt having a hi; surface area (a size of about 60 mesh or smaller). T resulting diesters can also be used under the stabilizi reaction mixture conditions of this invention as interm diates in processes for making ibuprofen by combini and reacting the α-acetyl-α'-methylsuccinate diesi with vinyl isobutyl ketone, (or the corresponding Ma nich base plus an alkylating agent) and an alkali me base for a time sufficient to form a reaction mixtu containing the α-methyl-α'-acetyl-α'-(5-methyl oxohexyl)succinate ester, which can then be convert to ibuprofen by procedures now known.

10 Claims, No Drawings

PROCESS FOR PREPARING ESTERS OF α-ACETYL-α'-METHYLSUCCINIC ACID AND ESTERS OF α-METHYL-α'-ACETYL-α'-(5-METHYL-3-OXOHEXYL)SUCCINIC ACID

CROSS-REFERENCE

This application is a continuation-in-part of application Ser. No. 778,571, filed Mar. 17, 1977, now abandoned.

INTRODUCTION

This invention relates to processes for preparing derivatives of succinic acid esters, and to the use of those succinate ester derivatives in processes for making useful acid compounds. More particularly, this invention provides an improved process for preparing esters of α-acetyl-α'-methylsuccinic acid, which are useful as intermediates for preparing esters of α-methyl-α'-acetyl-α'-(5-methyl-3-oxohexyl)succinic acid esters which are known to be useful in processes for preparing useful drug acids such as ibuprofen, flurbiprofen, and the like.

BACKGROUND OF THE INVENTION

It is known that diethyl α-acetyl-α'-methylsuccinate can be prepared in about 63 percent yield by reacting ethyl acetoacetate with ethyl α-bromopropionate in the presence of sodium hydroxide, potassium iodide and water. Chem. Abs. 62, 13037c abstracting (Zh. Pukl. Khim, 38(2), pp 436–7 (1965). Also, J. Chem. Soc. (London), 4633–40 (1970) reports that this same diester can be prepared in about 47 percent yield by reacting ethyl acetoacetate with ethyl α-bromopropionate in the presence of sodium in ethanol. Similar disclosures are found at Chem. Abs. 54, 10852h; Chem. Abs. 49, 1565c of J. Chem. Soc. (London) 3313 (1953); and Chem. Abs. 38, 2332 of J. Ind. Chem. Soc., 20, 173–7 (1943). However, it has been found in the studies which led to this invention that neither the aqueous basic system nor the ethanolic basic systems allowed the above alkylation to occur with the less expensive ethyl 2-chloropropionate in place of the ethyl 2-bromopropionate. I have found that using the 2-chloropropionate ester at moderate temperatures (40°–50° C.), no significant alkylation reaction was seen; under more vigorous (higher) temperature conditions, using these base systems, 2-chloropropionate and acetoacetate ester starting materials were consumed but little diethyl α-acetyl-α'-methylsuccinate ester accumulated in the product, evidencing that this valuable succinate ester intermediate is somewhat unstable and is further converted to undesired, useless by-products in those reaction mixtures. Those in process development research need and are seeking improved and more economical processes for preparing these esters and using them in preparing useful products.

For additional background to the use of α-acetyl-α-methylsuccinate esters in processes for preparing useful drug acid compounds, see British Pat. No. 1,265,800 and Belgian Pat. No. 820,267.

OBJECTS OF THE INVENTION

It is an object of this invention to provide an improved and more economical process for preparing esters of α-acetyl-α'-methylsuccinate acid.

It is a further object of this invention to provide a process for preparing esters of α-acetyl-α'-methylsuccinic acid under process conditions which minimize the decomposition of such ester product, which maximize the production and stability of such ester products in their reaction mixtures, and which permit the use of more economical starting materials.

It is a further object of this invention to provide an improved process for preparing α-methyl-α'-acetyl-α-(5-methyl-3-oxohexyl)succinate esters via the α-acetyl-α'-methylsuccinate diesters produced as described and claimed herein.

Other objects, aspects and advantages of this invention will become apparent from reading the specification and the claims which follow.

SUMMARY OF THE INVENTION

Briefly, by this invention I have discovered that esters of α-acetyl-α'-methylsuccinic acid can be prepared in improved yield under substantially anhydrous conditions from an acetoacetate ester and an α-chloro- or α-bromopropionate ester by alkylation reaction conditions which favor the formation of and which do not substantially degrade the α-acetyl-α'-methylsuccinate diester product to other less useful materials. The invention comprises reacting an ester of acetoacetic acid with an ester of one of these α-halopropionic acids in a substantially anhydrous nonpolar, aprotic organic liquid solvent medium in the presence of a solid/liquid phase transfer agent catalyst, a catalytic amount of an iodide ion and a substantially anhydrous, high surface area solid form of a deprotonating base, for a time sufficient to form the α-acetyl-α'-methylsuccinate base in the mixture. The resulting reaction mixture can be used per se in further chemical processing steps to contact and react the α-acetyl-α'-methylsuccinate ester content thereof with vinyl isobutyl ketone (or the corresponding Mannich base in the presence of an alkylating agent and an alkali metal base for a time sufficient to form the ester of α-methyl-α'-acetyl-α'-(5-methyl-3-oxohexyl succinic acid which is a non-cyclic aliphatic precursor to ibuprofen, a known drug acid, which is obtained by heat treatment according to procedures known in the art such as in British Pat. No. 1,265,800, Belgian Pat. No. 820,267, or in allowed U.S. application Ser. No. 622,130, filed Oct. 14, 1975.

DETAILED DESCRIPTION OF THE INVENTION

More specifically, this invention provides a process which comprises reacting an ester of acetoacetic acid with an ester of α-bromopropionic acid or α-chloropropionic acid in a substantially anhydrous mixture of nonpolar organic liquid solvent medium at a temperature of from about 50° C. to the reflux temperature of the mixture in the presence of a solid/liquid phase transfer agent, a catalytic amount of iodide ion and a substantially solid, substantially anhydrous form of deprotonating base reduced to a size of at least about 60 mesh, for a time sufficient to form the diester of α-acetyl-α'-methylsuccinic acid.

It has been found according to this invention that the above substantially anhydrous conditions provide the more stabilizing basic conditions needed for the formation of the α-acetyl-α'-methylsuccinate diesters from the more economical 2-chloropropionate esters. For example, it has been found that under otherwise identical conditions (78° C., K$_2$CO$_3$ as base, potassium iodide (KI) as iodide ion source, "Aliquat ®️ 336" as phase transfer agent), the diethyl α-acetyl-α'-methylsuccinate as a half-life of about 2 hours in absolute ethanol; in toluene (according to this invention) the half-life of this diester is extended to over 70 hours. Thus, we have found that alkylation of the acetoacetate ester with the 2-bromopropionate or 2-chloropropionate ester in toluene or heptane (or an equivalent nonpolar liquid organic medium), using dry, milled alkali metal carbonate, phase transfer catalyst and potassium iodide gives over 70 percent yield of the α-acetyl-α'-methylsuccinate diester with only 2.6 percent of o-alkylation and 2.9 percent formation of enol-lactone by-products. Using solvents such as methylene chloride for this process results in the formation of a reduced amount of α-acetyl-α'-methylsuccinate ester product contaminated with from 20 to 30 percent of o-alkylated material of the formula

(VII)

where Alk denotes the alkyl ester group, e.g., ethyl, which does not separate easily. It is best practice of the process of this invention to make the alkylation of the acetoacetate ester with the 2-bromopropionate or 2-chloropropionate ester to form the α-acetyl-α'-methylsuccinate diester as complete as possible.

Thus, the above chemistry provides an improved, practical chemical process by which important 2-arylalkanoic acid drug and agriculturally significant esters and acids therefrom can be prepared swiftly from inexpensive aliphatic component chemicals.

The acetoacetic acid ester starting materials are known compounds and the particular ester is not critical. See for example British Pat. No. 1,265,800. The ester should be one which is soluble in the substantially nonpolar, organic liquid medium. The $C_1$ to $C_6$-esters are preferred and the ethyl ester is more particularly preferred. Also, the α-bromopropionate and α-chloropropionate esters starting materials are known compounds, and the particular ester group is not critical but should be one which makes the ester compound soluble enough in the substantially nonpolar organic liquid solvent medium to react. The $C_1$ to $C_6$-alkyl esters, and particularly the ethyl ester, are preferred.

The substantially nonpolar organic liquids function as solvents for the ester reactants in the process of this invention and are organic liquid compounds or mixtures thereof which have dielectric constants of about 11 or below, preferably below 5, at 25° C. See, e.g., Lange's Handbook of Chemistry, 9th Edition, (1956), pp. 222–1225. Examples of solvent liquids for this purpose include benzene, toluene, xylene, cyclohexane, heptane, nonane, chloroform, bromobenzene, and the like. The preferred nonpolar, aprotic solvent for use herein is toluene and mixtures thereof.

The solid/liquid phase transfer agents are generally quaternary ammonium, sulfonium or phosphonium salts which function to assist contact between the solid and liquid materials in the mixture. Examples of such phase transfer agents include the tetra-($C_1$ to $C_{16}$-alkyl)ammonium halides such as tetrabutylammonium bromide, and other known quaternary salts available for this purpose, as well as crown ethers, e.g., those described in Cram U.S. Pat. No. 4,001,279, as well as the patent references cited therein, and sulfonium ($R_3S^+$) salts such as the tris($C_1$ to $C_{18}$-alkyl)sulfonium acid di($C_1$ to $C_{18}$-alkyl)phenylsulfonium salts, e.g., trimethylsulfonium iodide, trisdodecylsulfonium sulfate, dioctodecylmethylsulfonium chloride, dimethylphenylsulfonium nitrate, diundecyl-p-toluylsulfonium sulfate and the like, and phosphonium ($R_4P^+$) salts such as the tetra($C_1$ to $C_{18}$-alkyl)phosphonium and mixed alkyl arylphosphonium salts such as tetrabutylphosphonium chloride, trimethylphenylphosphonium iodide, methyl triphenylphosphonium sulfate, and the like. A commercially available example of such a phase transfer agent is sold under the tradename "Aliquat 336" which is believed to be tricaprylyl methylammonium chloride.

The iodide ion can be provided in any economical, soluble form in at least a catalytic amount. Alkali metal iodide salts such as sodium and potassium iodides are preferred. Ammonium iodide, and alkaline earth metal iodides such as calcium iodide, could also be used but are less preferred for reasons of cost and less efficiency with them. It can also be supplied by the iodide ion of a phase transfer agent salt, above. The catalytic amount of iodide ion can be a small amount, less than molar proportion to the ester reactants.

The deprotonating base such as alkali metal carbonates, orthophosphates, $C_1$ to $C_6$-alkoxides, hydroxides, and the like, (as opposed to Lewis bases generally), should be present in an amount at least about stoichiometrically equivalent to each of the ester reactants. The deprotonating base is preferably oven dried to remove at least most of any adhering water therefrom. It can be provided as a finely milled powder, usually below about 60 mesh, and preferably below about 100 mesh, or in some other high surface area contact form equivalent thereto, such as in highly porous pressed composite granules, tablets, pellets, or the like, which will act as the deprotonating base in these reaction mixtures.

The reaction mixture of the above ingredients is stirred or otherwise agitated to provide efficient contact of the liquid and solid components of the mixture for a time sufficient to effect as complete a reaction as is efficiently possible. Temperatures below 50° C. can be used, but below 50° C. the reaction times are generally too slow to be acceptable for commercial scale operations. Stirring the mixture for about six hours at about 75°–100° C. is generally about the optimum time and temperature for most efficient yields when the ethyl esters of the reactants are being used. Temperatures in the range of 90°–110° C. can be used.

The α'-acetyl-α'-methylsuccinate diester product can be recovered from the reaction mixture by conventional means, if desired, but since it is usually contemplated to use these esters as intermediates for further reaction, such recovery is usually not necessary.

Another advantage of preparing the α-acetyl-α'-methylsuccinate ester in the manner described herein is that it allows for the simple preparation of the α-acetyl-α-[(5-methyl-3-oxo)hexyl]-α'-methylsuccinate ester therefrom in the same vessel and solvent medium in which the α-acetyl-α'-methylsuccinate ester was prepared. The α'-acetyl-α'-[(5-methyl-3-oxo)hexyl]-α-methylsuccinate ester is described in Belgian Pat. No. 820,267, and is an intermediate which can be prepared in processes for preparing ibuprofen, a known commercially available anti-inflammatory drug acid. The method of this invention thus allows a complex chemical sequence to be carried out with minimum equipment and labor, according to a chemical reaction scheme which can be summarized by the following exemplary equations illustrating a preferred embodiment.

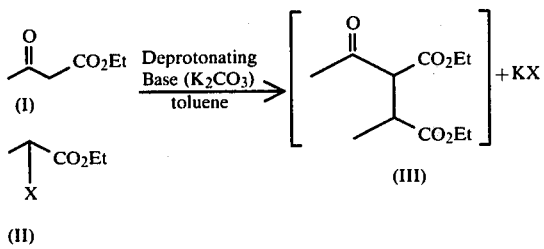

(1) isobutyl vinyl ketone; (2) KOH; (3) Polar solvent or

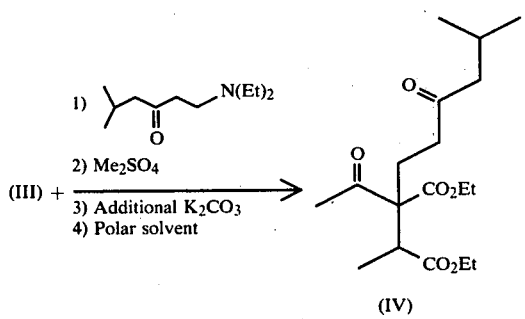

where Et denotes ethyl, X is chloro or bromo, and Me$_2$SO$_4$ is dimethylsulfate.

When the reaction of the acetoacetate ester (I) and the α-halopropionate ester (II) to form the α-acetyl-α'-methylsuccinate diester (III) in solution is completed, that mixture containing ester III can be treated with either isobutyl vinyl ketone per se and base plus a polar solvent or an N,N-di(C$_1$ to C$_6$-alkyl)-N-(5-methyl-3-oxohexyl)amine Mannich base precursor thereto (prepared by known procedures from a dialkylamine, paraformaldehyde and isobutyl methyl ketone) plus an alkylating agent such as a di(C$_1$ to C$_6$-alkyl)sulfate, e.g., dimethylsulfate, or a C$_1$ to C$_6$-alkyl iodide, e.g., methyl iodide, and additional deprotonating base which serves to convert the alkylated Mannich base to isobutyl vinyl ketone in situ as well as to catalyze the Michael reaction between the isobutyl vinyl ketone and the α-acetyl-α'-methylsuccinate diester derivative III in the presence of some added polar solvent, preferably a C$_1$ to C$_6$-alkanol or an N,N-bis-(C$_1$ to C$_6$-alkyl)formamide.

When the Mannich base, e.g., N,N-diethyl-N-(5-methyl-3-oxohexyl)amine, is added to the α-acetyl-α'-methylsuccinate diester to form the α-acetyl-α-(5-methyl-3-oxohexyl)-α'-methylsuccinate diester (IV), it is preferred to limit the additional deprotonating base, e.g. potassium carbonate, as closely as possible to not more than the amount which was used in the production of the α-acetyl-α'-methylsuccinate diester (III) itself. This is because at high (apparent) pH the α-acetyl-α'-methylsuccinate intermediate III is O-alkylated by the alkylating agent, e.g., dimethylsulfate. When the isobutyl vinyl ketone is being generated in situ, dimethylsulfate is preferably added at low temperatures, say 0° to 5° C., to suppress N,N-dialkyl-N-methylamine elimination which could occur at higher temperatures since it consumes dimethyl sulfate. Only after the Mannich base is quaternized and essentially absent (as determined by gas liquid chromatography or other equivalent analysis samples of the reaction mixture) is a more polar orga liquid solvent, preferably a C$_1$ to C$_6$-alkanol, e.g., etl nol, or an N,N-C$_1$ to C$_6$-dialkylformamide, and m deprotonating base, e.g., potassium carbonate, or pot sium hydroxide, added to initiate the Michael reacti between the Mannich base and the α-acetyl-α'-meth succinate diester (III). When added deprotonating b brings the apparent pH to about 11.5, the Michael re tion will occur. At about pH 13, aldolization (which acceptable) will occur. Addition of the polar solv such as a C$_1$ to C$_6$-alkanol, e.g., ethanol, is necessary Michael reaction. The addition of the polar solve e.g., alcohol, is made after quaternization of the M nich base is complete so that dimethyl sulfate is consumed by the alcohol or other polar solvent. T size (surface area), dryness and stirring of the protonating base, e.g., potassium carbonate, is imp tant to reproducibility of this heterogeneous reacti Control of these quaternization, base addition and po solvent addition factors is not difficult, however, o one is aware of the parameters discussed. We can p dict to within about 1 percent the amount of protonating base required to attain the pH to start Michael addition.

When the vinyl ketone intermediate, e.g., isobu vinyl ketone, used to make ibuprofen, is prepared distillation or by pyrolysis of the Mannich base hyd chloride [see British Pat. No. 1,265,800; Belgian I No. 820,267; and Tetrahedron Letters, 4739 (1968)], use of dimethyl sulfate is avoided. Distilled isobu vinyl ketone is also described by T. A. Spencer et "The Course of the Mannich Reaction with Met Isobutyl Ketone . . . " in J. Org. Chem. 32, 1234 (19( When the isobutyl vinyl ketone or other vinyl keton used directly, a rapid and efficient base catalyst for in this second step of the process is ethanolic potassi hydroxide which is added slowly to the nonpolar vent solution of the α-acetyl-α'-methylsuccinate dies The base, e.g., ethanolic potassium hydroxide, oper by converting the phase transfer agent, e.g., Aliquat or tetrabutylammonium bromide, used in the prep tion of the α-acetyl-α'-methylsuccinate diester (III) the quaternary ammonium hydroxide which prom the formation of the non-cyclic Michael adduct, dialkyl α-acetyl-α-(5-methyl-3-oxohexyl)-α'-methyl cinate (IV) used in the production of ibuprofen.

Continued base treatment of the reaction mix between the α-acetyl-α'-methylsuccinate diester ( and the isobutyl vinyl ketone to form the α-acetyl-α methyl-3-oxohexyl)-α'-methylsuccinate ester (IV) g an aldol condensation to form the respective ester 2-(4-isobutyl-2-oxo-cyclohex-3-enyl)propionic acid

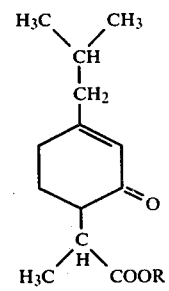

1 α-methyl-α'-(4-isobutyl-2-oxo-cyclohex-3-enyl)succinic acid (VI)

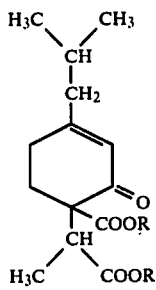

where R denotes the residue of the selected ester group and/or hydrogen for the corresponding acids per se which are also intermediates in the syntheses of ibuprofen. The non-cyclic diester IV can be isolated by known methods such as extraction and distillation. Esters IV, V or VI or any combination thereof and their free acids can then be used as intermediates to prepare ibuprofen. The intermediary of succinate diester (IV) for this purpose is implicit in British Pat. No. 1,265,800, and is explicit in Belgian Pat. No. 820,267. In addition, improved processes for using the succinate diester (IV) as an intermediate to prepare ibuprofen are described in co-owned U.S. patent application No. 622,130, filed Oct. 14, 1975, now U.S. Pat. No. 4,008,270 and U.S. patent application No. 689,366, filed May 24, 1976, now abandoned but replaced by a continuation-in-part application Ser. No. 777,598, filed Mar. 15, 1977, also now abandoned, but replaced with a continuation-in-part application Ser. No. 792,771, filed May 2, 1977.

The invention is further described and exemplified by the following detailed examples which are not intended to limit the scope of the invention.

EXAMPLE 1

Ethyl acetoacetate (75 mmoles, 9.51 ml.), ethyl α-chloropropionate (75 mmoles, 9.48 ml.), milled (about 80 mesh) potassium carbonate (13.8 g.), potassium iodide (1.0 g.), tetrabutylammoniumbromide (1.0 g.) and toluene (90 ml.) were placed in a 250 ml. 3-necked flask and stirred in a 100° C. bath for about 6 hours. Then a sample of the resulting reaction mixture was analyzed by the gas liquid chromatography (glc) assay method on a 6 foot, 2 percent OV 17 column and showed that 71.8 percent of the theoretical yield of diethyl α-methyl-α'-acetylsuccinate had been produced. This toluene solution of diethyl α-methyl-α'-acetylsuccinate is useful directly in processes for preparing other useful compounds such as ibuprofen which are known anti-inflammatory drug acid compounds.

EXAMPLE 2

Preparation of diethyl α-acetyl-α'-methylsuccinate, and use of the reaction mixture of this ester to form diethyl α-methyl-α'-(5-methyl-3-oxohexyl)-α'-acetylsuccinate A 1.0 g. portion of Aliquat 336 (tricaprylyl methyl ammonium chloride), 35.0 ml. of toluene, 9.51 ml. (75 mmole) of ethyl acetoacetate, 9.48 ml. (75 mmole) of ethyl chloropropionate, 1.0 g. (<60 mesh) of potassium iodide, and 100 milliequivalents, 13.8 g. of less than 80 mesh, oven-dried potassium carbonate are placed in a 250 ml. 3-necked flask equipped with a condenser, mechanical stirrer and thermometer. The mixture is stirred at 75°–80° C. for about 6 hours to ensure formation of diethyl α-acetyl-α'-methylsuccinate, without substantial decomposition by further heating.

Then 7.5 ml. of ethanol is added and the mixture is cooled to 0° C. Mannich base, N,N-diethyl-N-(5-methyl-3-oxohexyl)amine, 90 percent pure, 20.0 ml., is added. Dimethylsulfate, 16.0 ml. (172 mmole) is added over 1.3 hours while controlling the temperature to below about 3° C. The mixture is stirred for 5 hours and 20 minutes as the temperature was allowed to rise gradually from 0° to 31° C. in about 62 minutes and then cooled again to 20° to 24° C. over 4 hours while 8.8 g. of potassium carbonate is added in four portions (at 24 minutes, 44 minutes, 1 hour and 10 minutes, and 1 hour and 40 minutes) from the reaction starting time. After overnight storage at −5° C. the mixture is stirred again at 15°–20° C. for two hours to ensure as complete a reaction as possible.

For workup, the resulting reaction mixture is mixed with 50 ml. of water and the aqueous and organic phases were allowed to separate. The aqueous phase is washed with 40 ml. of toluene. The toluene phases are washed with two 35 ml. portions of saturated brine (NaCL) solution. Additional 3rd, 4th and 5th washes with saturated brine solution (22 ml. each) are also conducted to more completely neutralize the organic phase product mixture (the pH was lowered from 12.6 to 6.5 by these washes). These additional washes are not essential. The toluene phases are combined, dried with sodium sulfate, concentrated and distilled. The distillate is collected in five fractions; fractions 2, 3 and 4, b.p. 154°–176° C., are taken as containing the product in a total weight of 19.074 g. for these fractions, or 50.8 mmole (67.7 percent yield, based on ethyl acetoacetate), of diethyl α-methyl-α'-(5-methyl-3-oxohexyl)-α'-acetylsuccinate. Alternatively, crude non-distilled mixture product can be used directly in ibuprofen synthesis.

EXAMPLE 3

Preparation of diethyl α-methyl-α'-acetyl-α'-(5-methyl-3-oxohexyl)succinate from diethyl α-acetyl-α'-methylsuccinate and prepared vinyl isobutyl ketone To a 105.5 ml. (50 mmole) solution of diethyl α-acetyl-α'-methylsuccinate in toluene, prepared as described in Example 2 in a 250 ml. 3-necked flask there was added 28.0 ml. (100 mmole) of vinyl isobutyl ketone in a 49.3 percent solution, 0.813 g./ml. Then 8.0 ml. of a 101 mg./ml. solution of potassium hydroxide (14.4 m equivalents) in ethanol was added. The mixture was stirred for 6 hours at room temperature and then 2.5 ml. (4.5 m equivalents) of the same ethanolic potassium hydroxide solution was added and the reaction was allowed to continue for 4 more hours.

Saturated brine (25 ml.) and water (5 ml.) were added and the phases were separated. The toluene phase was washed with brine (30 ml.) and then with brine (30 ml.) containing 0.27 g. of sodium bisulfate. Aqueous phases were backwashed in sequence with toluene (30 ml.). The combined toluene phases were dried over sodium sulfate, filtered and concentrated to an oil weighing 26.63 g. The oil was distilled and the distillate was collected in three fractions.

| Fraction | Oil Bath, T°C. | B.P., °C. | Pressure, mm.Hq | Wt. q. |
|---|---|---|---|---|
| 1 | <100 | <50° | 0.30–0.32 | 0.183 |
| 2 | <160 | 90°–128° | 0.28–0.30 | 0.280 |

-continued

| Fraction | Oil Bath, T°C. | B.P., °C. | Pressure, mm.Hq | Wt. q. |
| --- | --- | --- | --- | --- |
| 3 | 180–215 | 155–185 | 0.22–0.30 | 18.172 |

Analysis of fraction 3 by gas liquid chromatography showed that it contained (a) 7.59 mmole of ethyl 2-(4-isobutyl-2-oxo-cyclohex-3-enyl)propionate; (b) 23.30 mmole of diethyl α-methyl-α'-acetyl-α'-(5-methyl-3-oxohexyl)succinate; and (c) 11.94 mmole of ethyl 2-(4-isobutyl-2-oxo-1-carboethoxy-cyclohexenyl)propionate, or a total of 42.89 mmole of 85.8 percent yield. A residue of 2.20 g. remained.

Each of these products (a), (b) and (c) (separately or in a mixture) in the fraction 3 mixture can be converted to the useful drug acid, ibuprofen, by known procedures, and thus the whole of fraction 3 would be used for that purpose.

Alternatively, the crude undistilled mixture of (a), (b) and (c) can be converted directly to ibuprofen by the heat treatment procedures referred to above.

In summary, this invention provides a process improvement in which α-acetyl-α'-methylsuccinate esters can be produced in a stabilizing reaction medium which permits the use of mild, substantially anhydrous conditions as well as the use of the less reactive α-chloropropionate esters as starting material. The process conditions favor the formation of the α-acetyl-α'-methylsuccinate ester intermediates while minimizing its decomposition which lowers yields of the desired α-acetyl-α'-methylsuccinate ester intermediates, and the desired products resulting therefrom.

The term "substantially anhydrous" means that reasonable care is used in the choice of solvent and reagents as they do not contain large amounts of water. A possible exception is in the case of phase transfer catalyst materials which can be used and which often contain and come supplied with a small amount of water of hydration or adhering water, but since these catalysts are used in only small amounts, the water added to the total reaction mixture volume as a result of their use is only a fraction of a percent by volume.

I claim:

1. A process which comprises reacting an ester of acetoacetic acid with an ester of α-halopropionic acid wherein halo is chloro or bromo in a substantially anhydrous mixture of a non-polar, aprotic organic liquid having a dielectric constant below about 11 at 25° C. at a temperature of from about 50° C. to the reflux temperature of the mixture in the presence of a phase transfer agent, a catalytic amount of an iodide ion and a deprotonating base having a surface area equivalent to a size below at least about 60 mesh, for a time sufficient to form the diester of α-acetyl-α'-methylsuccinic acid.

2. A process according to claim 1 wherein the nonpolar, aprotic organic liquid has a dielectric constant below about 5 at 25° C.

3. Process according to claim 2 wherein ethyl acetoacetate and ethyl α-halopropionate are heated together in a liquid medium containing benzene, toluene or xylene in the presence of potassium carbonate, potassium iodide, and tetrabutylammonium bromide at 90° to 110 C. for a time sufficient to form diethyl α-acetyl-α' methylsuccinate.

4. Process according to claim 1 wherein the ester radicals of the acetoacetate and the α-halopropionate esters are $C_1$ to $C_6$-alkyl radicals.

5. Process according to claim 4 wherein ethyl chloropropionate is reacted with ethyl acetoacetate in a toluene mixture containing tricaprylyl methylammonium chloride as phase transfer agent, potassium iodide a iodide ion source, potassium carbonate, milled to below about 80 mesh as deprotonating base at 75° to 80° C. fo a time sufficient to form diethyl α-acetyl-α'-methylsuccinate.

6. Process according to claim 1 which further includes the steps of combining and reacting the α-acetyl α'-methylsuccinate diester with isobutyl vinyl ketone and base in a polar solvent for a time sufficient to form a mixture containing the diester of α-methyl-α'-acetyl α'-(5-methyl-3-oxohexyl)succinic acid.

7. Process according to claim 6 wherein a nonpolar aprotic organic liquid mixture containing a di($C_1$ to $C_6$-alkyl)ester of α-acetyl-α'-methylsuccinic acid i combined and reacted with vinyl isobutyl ketone and $C_1$ to $C_6$-alkanol solution of a base for a time sufficien to form a mixture containing a di-$C_1$ to $C_6$-alkyl α-methyl-α'-acetyl-α'-(5-methyl-3-oxohexyl)succinate ester.

8. Process according to claim 7 wherein a toluen solution of diethyl α-acetyl-α'-methylsuccinate is combined and reacted with vinyl isobutyl ketone and potassium hydroxide in ethanol for a time sufficient to form a mixture containing diethyl α-methyl-α'-acetyl-α'-(5 methyl-3-oxohexyl)succinate.

9. Process according to claim 6 wherein preformed isobutyl vinyl ketone is added per se to the mixtur containing α-acetyl-α'-methylsuccinate diester.

10. Process according to claim 6 wherein the isobutyl vinyl ketone reactant is formed in situ by adding to th mixture containing the α-acetyl-α'-methylsuccinat diester an N,N-bis($C_1$ to $C_6$-alkyl)-N-(5-methyl-3 oxohexyl)amine, an alkylating agent and a deprotona ing base.

* * * * *